United States Patent
Wenstrom, Jr.

[11] Patent Number: 6,152,928
[45] Date of Patent: Nov. 28, 2000

[54] LIGAMENT FIXATION DEVICE AND METHOD

[75] Inventor: Richard F. Wenstrom, Jr., Norwood, Mass.

[73] Assignee: Ethicon, Inc., Somerville, N.J.

[21] Appl. No.: 09/261,308

[22] Filed: Mar. 2, 1999

[51] Int. Cl.[7] .................................................. A61B 17/84
[52] U.S. Cl. ........................ 606/72; 606/77; 606/151; 606/232; 623/13
[58] Field of Search ................. 606/72, 75, 88, 606/151, 232; 623/13

[56] References Cited

U.S. PATENT DOCUMENTS

| | | | |
|---|---|---|---|
| 4,828,562 | 5/1989 | Kenna | 623/13 |
| 4,870,957 | 10/1989 | Goble et al. | |
| 4,950,270 | 8/1990 | Bowman et al. | 606/72 |
| 4,997,433 | 3/1991 | Goble et al. | 606/64 |
| 5,108,431 | 4/1992 | Mansat et al. | 623/13 |
| 5,147,362 | 9/1992 | Goble | 606/72 |
| 5,356,413 | 10/1994 | Martins et al. | 606/75 |
| 5,356,435 | 10/1994 | Thein | 623/15 |
| 5,372,604 | 12/1994 | Trott | 606/232 |
| 5,456,721 | 10/1995 | Legrand | 623/13 |
| 5,501,696 | 3/1996 | Trott | 606/232 |
| 5,571,184 | 11/1996 | DeSatnick | 623/13 |
| 5,618,314 | 4/1997 | Harwin et al. | 606/232 |
| 5,632,748 | 5/1997 | Beck, Jr. et al. | 606/89 |
| 5,643,266 | 7/1997 | Li | 606/72 |
| 5,645,588 | 7/1997 | Graf et al. | 623/13 |
| 5,707,395 | 1/1998 | Li | 606/232 |
| 5,766,250 | 6/1998 | Chervitz et al. | 623/13 |
| 5,769,894 | 6/1998 | Ferragamo | 623/13 |
| 5,785,714 | 7/1998 | Morgan et al. | 606/86 |

*Primary Examiner*—Michael Buiz
*Assistant Examiner*—David O. Reip
*Attorney, Agent, or Firm*—Nutter, McClennen & Fish, LLP

[57] ABSTRACT

An anchor for securing soft tissue within a bone tunnel having an inner wall includes a resilient body member that defines a soft tissue opening and has a first, leading end and a second, trailing end. The anchor also has at least one bone engaging element connected to the body member. The anchor is movable between a first, sliding position wherein the at least one bone engaging element slides along the inner wall of the bone tunnel and the anchor is movable within the bone tunnel, and a second, locking position wherein the at least one bone engaging element engages the inner wall of the bone tunnel to resist movement of the anchor within the bone tunnel. In one embodiment, two opposed bone engaging legs are connected to the body at the second trailing end and extend at an angle away from the longitudinal axis and in a direction from the leading end to the trailing end. A pull tool engaging element provided on the second, trailing end of the body between the two opposed bone engaging legs.

17 Claims, 5 Drawing Sheets

LIGAMENT FIXATION DEVICE AND METHOD

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to a device and method for attaching soft tissue such as a ligament or ligament graft to a bone. The device and method are particularly useful for fixing the soft tissue within a tunnel formed in a bone proximate to the natural point of attachment of the soft tissue.

The complete or partial detachment of ligaments, tendons or other soft tissues from their associated bones within the body are relatively commonplace injuries, particularly among athletes. Such injuries are generally the result of excess stress being placed on these tissues. Tissue detachment may occur as the result of an accident such as a fall, overexertion during a work related activity, during the course of an athletic event or in any one of many other situations and/or activities. If, however, the ligament or tendon is completely detached from its associated bone or bones, or if it is severed as part of a traumatic injury, partial or permanent disability may result. Fortunately, a number of surgical techniques; exist for reattaching such detached tissues and/or completely replacing severely damaged tissues.

One such technique involves the reattachment of the detached tissue using "traditional" attachment devices such as metal staples and cancellous bone screws. Such "traditional" attachment devices have also been used to attach tendon or ligament substitutes (often formed of autogenous tissue harvested from elsewhere in the body) to the desired bone or bones.

Another technique is described in detail in U.S. Pat. No. 4,950,270 entitled "Cannulated Self-Tapping Bone Screw", issued to Bowman et al. on Aug. 21, 1990, and specifically incorporated herein by reference. In this technique, the anterior cruciate ligament in a human knee, for example, is replaced and/or repaired by forming bone tunnels through the proximal tibia and/or distal femur at the points of normal attachment of the anterior cruciate ligament. A ligament graft with a bone block on at least one of its ends is sized to fit within the bone tunnels. A suture is then attached to the outer end of each bone plug and sutures on opposite ends of the graft structure are passed through the femoral and tibial bone tunnels. The femoral plug and the tibial plug are then inserted into their respective bone tunnels behind the sutures. The sutures are then drawn tight simultaneously in opposite directions. This procedure places the bone plugs in the desired position, and imparts the desired degree of tension to the ligament or ligament substitute. Finally, a bone screw is inserted between each bone plug and the wall of its associated bone tunnel so as to securely lock the bone plug in position by a tight interference fit.

Another common ligament attachment technique is described in U.S. Pat. No. 5,645,588 entitled "Graft Attachment Device," issued to Graf et al. on Jul. 8, 1997, and in U.S. Pat. No. 5,769,894 entitled "Graft Attachment Device and Method of Attachment," issued to Ferragamo on Jun. 23, 1998. This method uses a button-like device that rests on the outside of a bone, covering at least part of the opening to a bone tunnel. The button is first sutured to a portion of a ligament graft at a distance from the button, in effect suspending the graft from the button. The button-suture-graft construct is then pulled through the bone tunnel and the button is seated outside the far end of the tunnel with the ligament graft suspended within the tunnel.

U.S. Pat. No. 5,356,413, entitled "Surgical Anchor and Method for Deploying the Same," issued to Martins et al. on Oct. 18, 1994, discloses a surgical anchor device having a metal anchor body with nickel-titanium alloy arcs located on a leading end of the body. One transverse bore on the leading end is used to place a suture which is used to pull the anchor into a bone tunnel. A second transverse bore located in the trailing end of the anchor. The ligament graft may be directly connected to the second bore, or the ligament graft may be suspended from the second bore by suture thread.

The ligament fixation schemes described above have not been entirely successful. For example, rigid attachment using "traditional" attachment devices such as staples, sutures and screws often cannot be maintained even under normal tensile loads. Also, the use of sharp screws to create a locking interference fit between a bone plug and a bone tunnel can be problematic. For one thing, there is always the possibility of damaging the ligament during insertion of the screw. In addition, it can be difficult to maintain the desired tension on the ligament or repair material during insertion of the screw.

Non-rigid fixation schemes, such as suspending a ligament graft from a suture button, also have drawbacks. Because the graft structure is not rigidly fixed within the bone tunnels, movement of the graft structure can disrupt the healing process.

Despite the various ligament fixation methods known in the art, it would still be desirable to provide a ligament fixation device and method that can rigidly fix a ligament graft within a bone tunnel at a desired ligament tension for a time sufficient to allow the ligament graft to permanently fix itself to the bone.

SUMMARY OF THE INVENTION

The present invention provides an anchor for securing soft tissue within a bone tunnel having an inner wall. The anchor includes a resilient body member that defines a soft tissue opening and has a first, leading end and a second, trailing end. The anchor also has at least one bone engaging element connected to the body member. The anchor is movable between a first, sliding position wherein the at least one bone engaging element slides along the inner wall of the bone tunnel and the anchor is movable within the bone tunnel, and a second, locking, position wherein the at least one bone engaging element engages the inner wall of the bone tunnel to resist movement of the anchor within the bone tunnel.

In one embodiment, the anchor of the invention is bioabsorbable and includes a resilient body defining a soft tissue opening and having a longitudinal axis, a first leading end and a second trailing end. Two opposed bone engaging legs are connected to the body at the second trailing end and extend at an angle away from the longitudinal axis and in a direction from the leading end to the trailing end. A pull tool engaging element is provided on the second, trailing end of the body between the two opposed bone engaging legs.

The anchor body can be resilient and can deform in order to move from the first to the second position in order to lock within a bone tunnel. In particular, the anchor body may deform in the area between the opposed bone engaging legs at the trailing end of the anchor body and cause the legs to extend farther outward to engage the wall of the bone tunnel.

The anchor body can take the form of a broken circle having a break or gap at the leading end. As the anchor deforms from the first to the second position, the gap in the anchor body closes, and when closed, the anchor body resists further deformation. Stabilizing legs may also be provided on the anchor body on opposite sides of the gap.

The anchor may deform from the first to the second position as a result of forces applied on the anchor such as tension on the soft tissue being anchored and engagement of tips at the end of the bone engaging legs with the walls of the bone tunnel.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
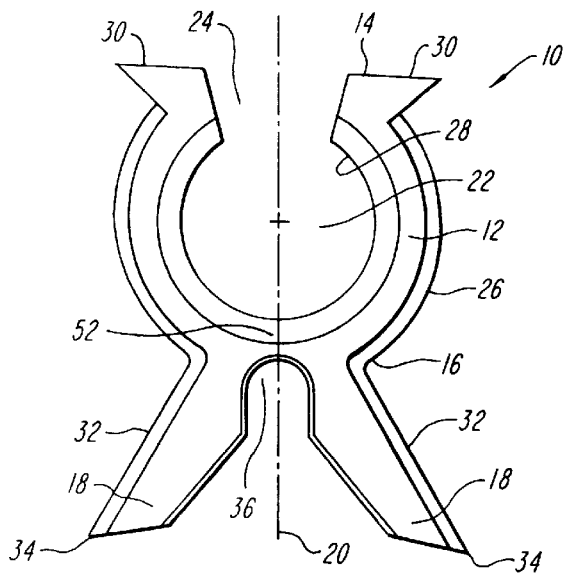
FIG. 1 illustrates an anchor of the invention.
Figure 2:
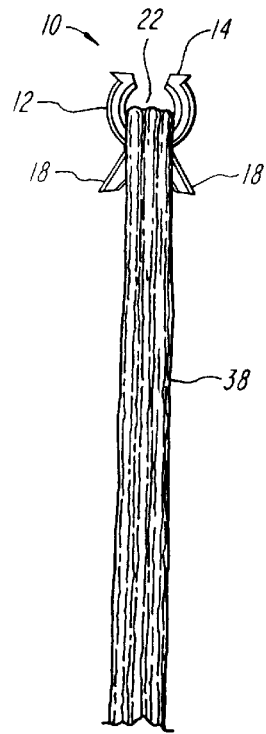
FIG. 2 illustrates the anchor of FIG. 1 engaged with a ligament.

An anchor 10 of the invention having a body 12 and at least one bone engaging element 18 is illustrated in FIGS. 1 and 2. The body 12 has a leading end 14 and a trailing end 16, the at least one bone engaging element 18 being connected to the body 12 in proximity to the trailing end. A longitudinal axis 20, generally coincident with the axis of a bone tunnel with which anchor 10 may be used, extends through the leading and trailing ends 14, 16.

Body 12 is generally in the form of an incomplete circle having a transverse opening 22 sized to receive a ligament graft and a break or gap 24 in the circle at the leading end 14 of the body 12. Transverse opening 22 is sized to receive a ligament graft and may generally be about 0.240 inch in diameter. The outer surface 26 of body 12 is rounded and the inner surface 28 of body 12 is chamfered so as not to present sharp edges that might damage a ligament graft. The leading end 14 of body 12 may include stabilizing legs 30 provided adjacent to gap 24.

Exemplary anchor 10 has two opposed bone engaging members 18. These bone engaging members 18 are attached to a body 12 at its trailing end 16 and extend outward away from longitudinal axis 20 and downward in a direction from the leading edge 14 toward the trailing edge 16 of the body 12. On anchor 10, the outer surface 32 of each bone engaging member 18 extends at an angle of about 30° with the longitudinal axis 20 and ends at a point 34 that is suitable to engage the inside of a bone tunnel to hold anchor 10 in place.

A pulling element 36 is provided on the anchor of the invention so that a tool, such as a length of suture thread, can engage the anchor for the purpose of pulling it, and an attached ligament graft, through a bone tunnel for fixation. On anchor 10, the pulling element 36 is a slot defined between the bone engaging elements 18 at the trailing end 16 of body 12.

Exemplary anchor 10 is formed from a resilient material that can be bioabsorbable. Exemplary non-absorbable materials for forming anchor 10 include delrin and polysulfone. Bioabsorbable polymers or copolymers may be selected according to the desired adsorption or degradation time. That time, in turn, depends upon the anticipated healing time for the reattachment of soft tissue to the bone or other tissue which is the subject of the surgical procedure. Known biodegradable polymers and copolymers range in degradation time from about three months for polyglycolide to about forty-eight months for polyglutamic-coleucine. A common biodegradable polymer used in absorbable sutures is an absorbable copolymer derived from glycolic and lactic acids, such as a synthetic polyester chemically similar to other commercial available glycolide and lactide copolymers. Glycolide and lactide, in vivo, degrade and absorb by hydrolysis into lactic acid and glycolic acid which are then metabolized by the body.

Exemplary anchor 10 is a unitary anchor and leg structure formed from a resilient material. It is generally sized that it can slide snugly within a bone tunnel to which a ligament is being fixed. In one embodiment, body 12 has a diameter of about 0.400 inches and a depth of about 0.160 inches. The span of bone engaging legs 18 from tip 34 to tip 34 is about 0.460 inches. The leg span may be greater than the diameter of the bone tunnel in which anchor 10 will be used, causing bone engaging legs 18 to flex inward when entering the tunnel. The circular wall of body 12 has a thickness of about 0.080 inches. The thickness of body 12 in region 52 between pulling element 36 and transverse opening 22 is about 0.0495 inches. Generally, an anchor 10 having these dimensions can conveniently be used in a bone tunnel having a diameter of about 0.400 inches.

As illustrated in FIG. 1, resilient anchor 10 is in a first, sliding position in which anchor 10 is undeformed. As will be explained in greater detail below, resilient anchor 10 deforms in use into a second, locking position in which anchor 10 no longer slides in the direction of tension from the ligament, but is locked to the inner surface of a bone tunnel.

In FIG. 2, anchor 10 is shown engaged with a ligament graft 38 which passes through transverse opening 22. Ligament graft 38 can be an actual ligament, it could also be fashioned from other soft tissue (such as a portion of a patella tendon), or it could be synthetic. Ligament graft 38 can be secured to anchor 10 by passing an end of ligament graft 38 through transverse opening 22 and suturing the ligament end back to the ligament 38. Attachment means other than sutures, including staples or clips for example, can also be used to secure ligament 38 through transverse opening 22. Because transverse opening 22 is transverse to the direction of bone engaging legs 18, ligament 38 will not catch on bone engaging legs 18.

Figure 3:
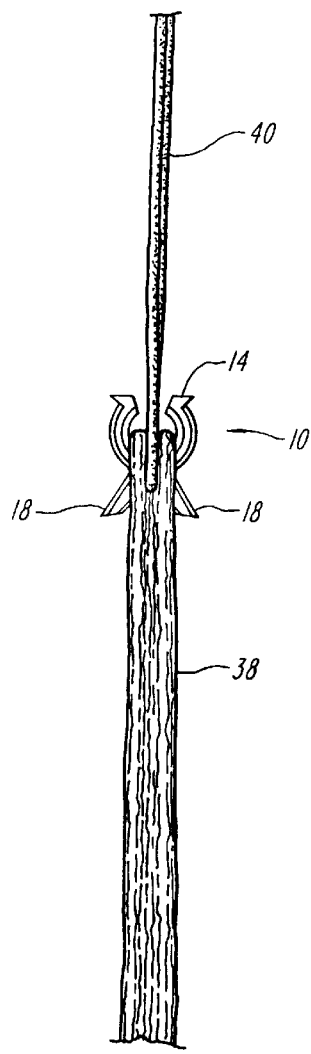
FIG. 3 illustrates the anchor of FIG. 1 engaged with a ligament and a suture.

A length of suture 40 is also engaged with anchor 10 as illustrated in FIG. 3. Suture 40 may be attached to anchor 10 before or after ligament graft 38 is secured. Suture 40 passes through pulling element 36 (FIG. 1) and each end of suture 40 extends from the pulling element 36 past the leading end 14 of anchor 10. If suture 40 is attached to anchor 10 after ligament 38 is secured thereto, suture 40 can be attached by attaching one end to a needle and passing the needle and suture 40 through ligament 38, through pulling element 36, and through ligament 38 on the opposite side of pulling element 36.

Application of the structure of FIG. 3, that is, anchor 10 having a ligament graft 38 and a length of suture 40 affixed thereto, to fix ligament graft 38 within a bone tunnel is illustrated in FIGS. 4 to 7. In these figures, a bone tunnel 42, shown in cut away, has been formed in a proximal tibia 44 and distal femur 46. Exemplary tunnel 42 passes through the normal attachment points of an anterior cruciate ligament in a normally functioning human knee, however, the methods and devices of the invention can be used to affix other ligaments or other soft tissues or soft tissue substitutes to bone.

Figure 4:
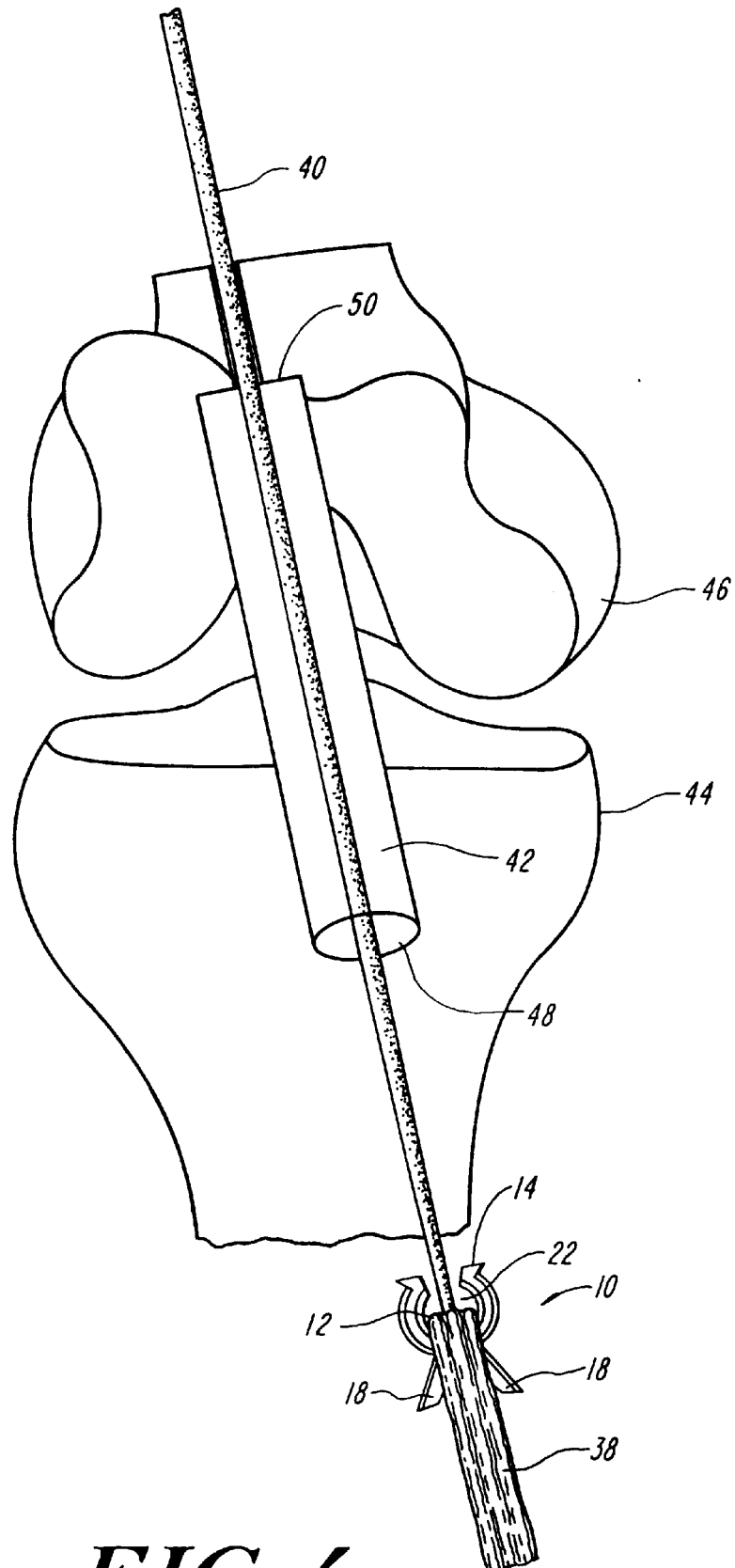
FIG. 4 illustrates, with partial cut away, the anchor of FIG. 1 engaged with a ligament and a suture and being drawn toward a bone tunnel in a patient's proximal tibia and distal femur.
Figure 5:
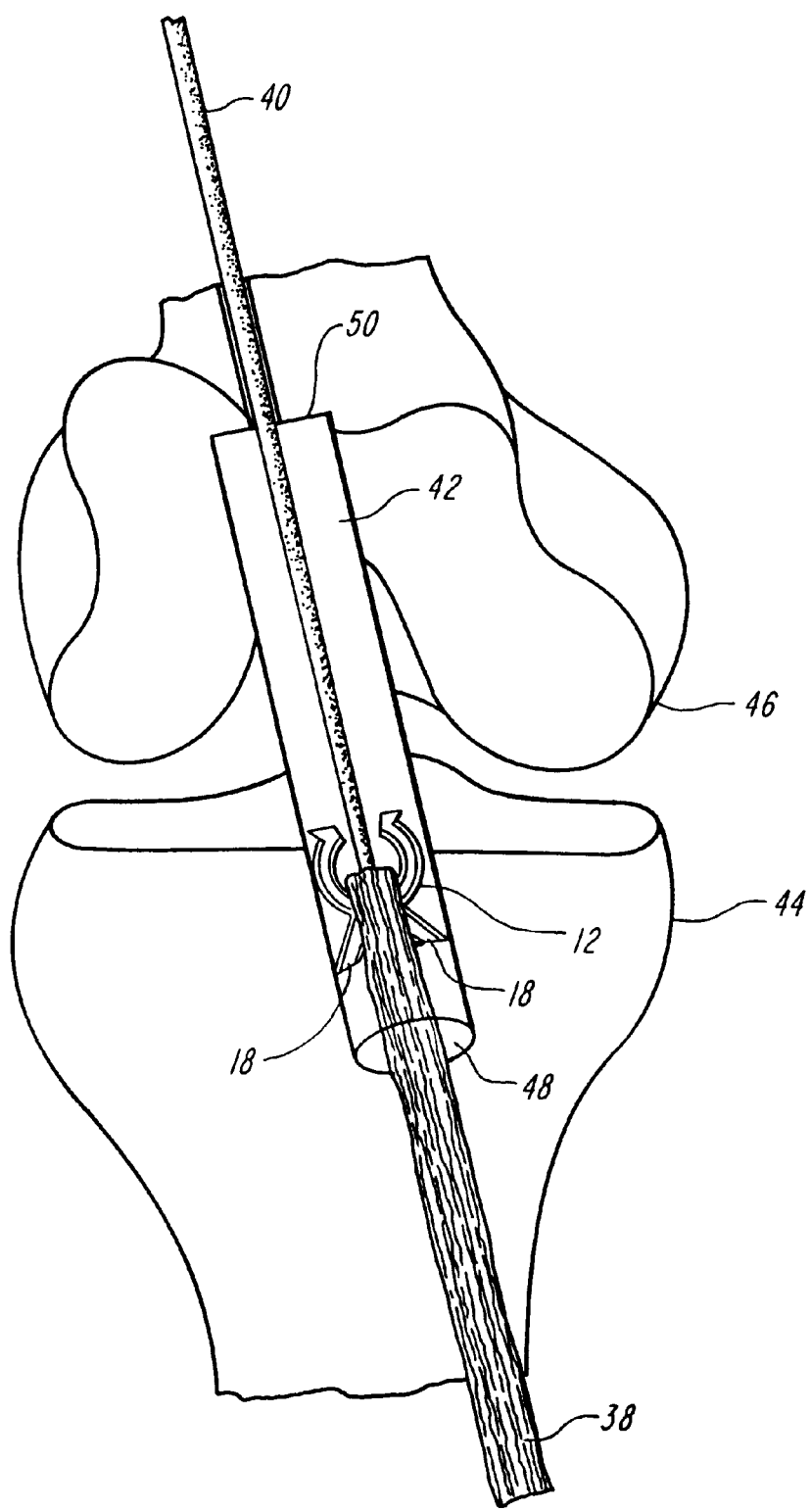
FIG. 5 illustrates, with partial cut away, the anchor of FIG. 1 engaged with a ligament and a suture and being drawn through a bone tunnel in a patient's proximal tibia and distal femur.
Figure 6:
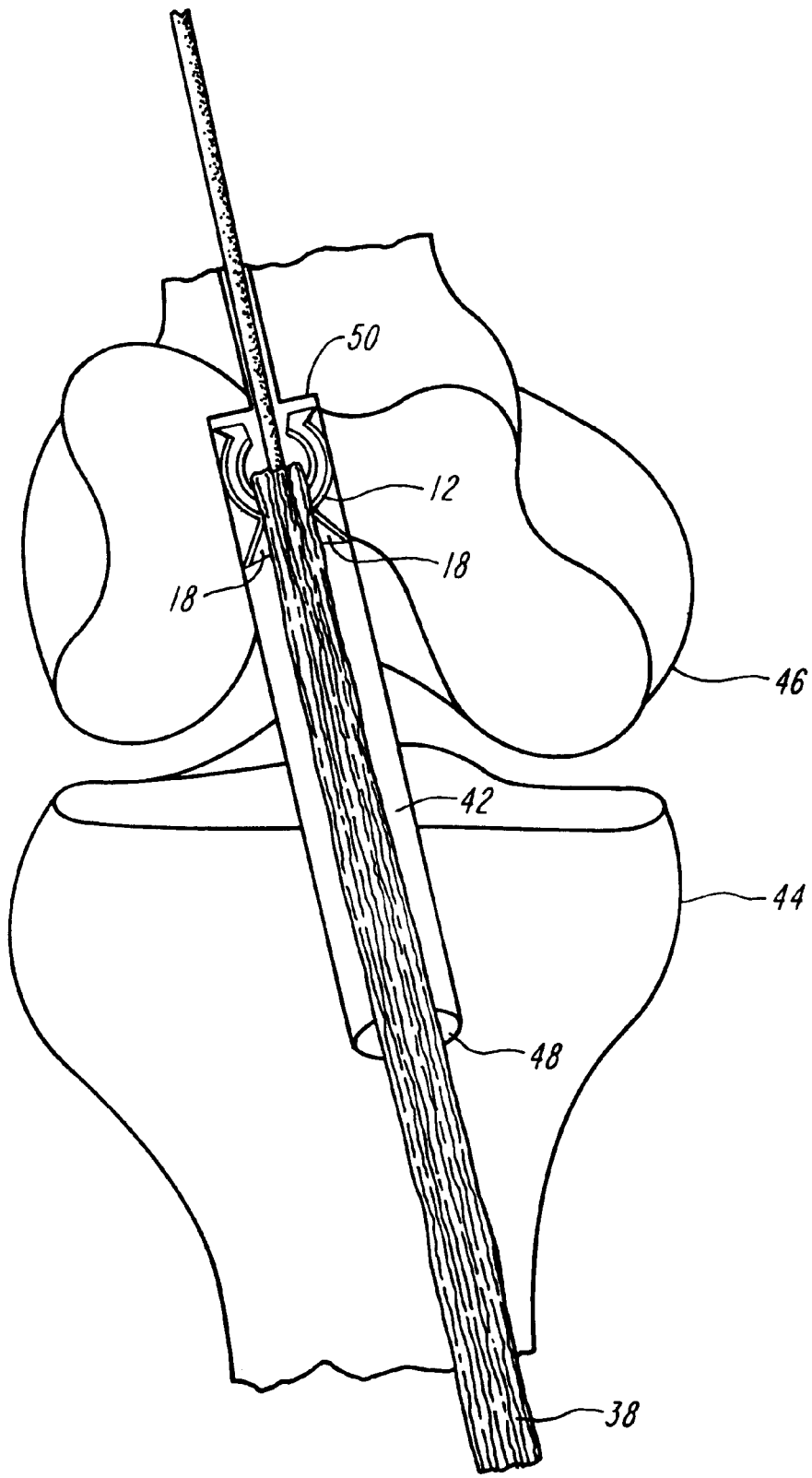
FIG. 6 illustrates, with partial cut away, the anchor of FIG. 1 engaged with a ligament and a suture and fully drawn into a bone tunnel in a patient's proximal tibia and distal femur.
Figure 7:
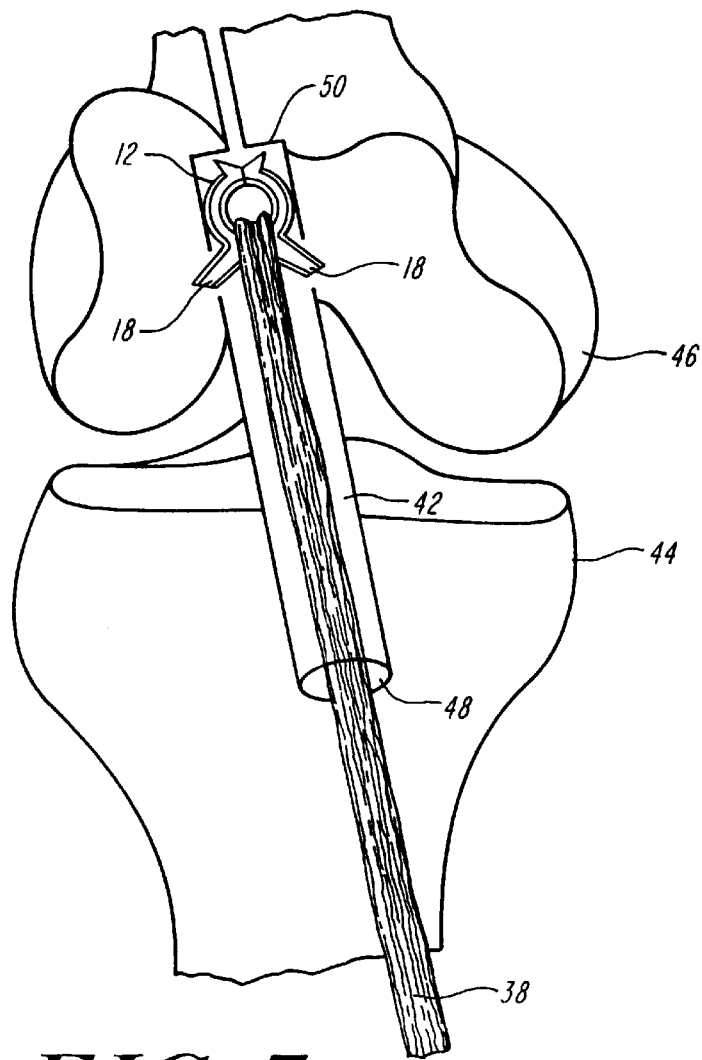
FIG. 7 illustrates, with partial cut away, the anchor of FIG. 1 engaged with a ligament after a suture has been removed and the anchor has deformed into a locking position within a bone tunnel in a patient's proximal tibia and distal femur.

As shown in FIG. 4, fixation of ligament 38 within bone tunnel 42 can begin by drawing suture 40 into the distal end 48 of bone tunnel 42 in the tibia, proximally through the tunnel 42, and out the proximal end 50. As shown in FIG. 5, anchor 10 and ligament 38 can be drawn into bone tunnel 42 by pulling on suture 40. It may be desirable for a surgeon to apply a tension on ligament 38 during this process so that ligament 38 remains firmly seated in transverse opening 22 of anchor 10. Anchor 10 slides snugly within tunnel 42 and the outer surface 32 of each bone engaging leg 18 may contact the inner surface of tunnel 42 as anchor 10 slides therein. When anchor 10 reaches the desired location for fixation, illustrated in FIG. 6, the surgeon may stop pulling on suture 40 and thus stop sliding anchor 10 proximally into tunnel 42.

Figure 8:
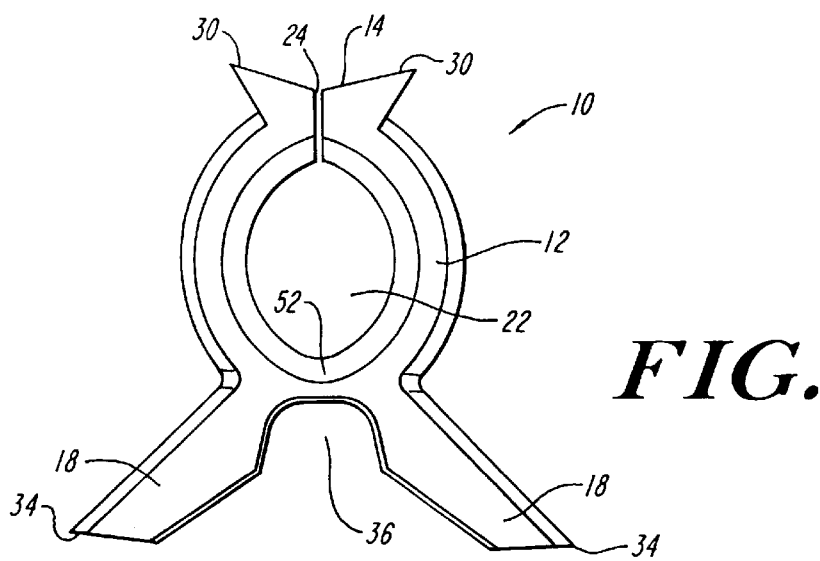
FIG. 8 illustrates the anchor of FIG. 1 deformed into a locking position.

When the anchor has reached, or slightly passed, the desired position, tension on suture 40 can be released while tension on ligament 38 is applied or maintained. With suture 40 tension removed and tension applied to ligament 38, anchor 10 deforms into a second, locking position illustrated in FIGS. 7 and 8. The tension applied though ligament 38 causes the tips 34 of legs 18 to engage the inner surface of bone tunnel 42. The tension on ligament 38 continues to pull on anchor 10, causing the anchor to deform. Legs 18 angle more acutely to extend legs 18 outward into bone. Simultaneously, body 12 deforms as its broken circle shape deforms to look more like a completed oval (see FIG. 8). When designed as shown in FIGS. 1 and 8, much of the deformation of anchor 10 from its first, sliding position to its second, locking position occurs in the region 52 between pulling element 36 and transverse opening 22 as this region of anchor 10 has the smallest cross sectional area. Anchor body 12 can be configured, by sizing the gap 24 in the broken circle body 12, to allow a controllable amount of deformation before the gap 24 closes and the portions of anchor body 12 adjacent to stabilizing legs 30 meet. At this point, anchor 10, and thus ligament 38, is locked against distal movement, i.e. motion in the direction of ligament 38 tension.

With the anchor 10 fixed in the desired position, suture 40 may be removed by cutting suture 40 or by pulling on one end to slide suture 40 out of contact with ligament 38 and with anchor 10.

It is also possible, using the method and device of the invention, to adjust the position of the anchor 10 even after it has be locked into position. By pulling on suture 40 before it is removed, the anchor 10 can be pulled proximally within tunnel 42 and will resume its first, sliding position. If the new desired position is proximal, suture 10 can be pulled until the anchor reaches that position. If the new desired position is distal, the anchor 10 can be unlocked by pulling on the suture 40, then moved distally by supplying equal tension on the ligament while carefully sliding the anchor 10 in the distal direction.

The distal end of ligament 38 can be fixed within the tibial portion of tunnel 42 by any means known in the art including use of another anchor 10, use of other prior art anchors, staples, screws, or interference screws where a b)ne block is provided on the distal end of the ligament 38.

Anchor 10 of the invention can also be used with a ligament having a bone block on the proximal, and if desired also on the distal, end thereof. Similarly to the embodiment illustrated in FIGS. 8 and 9 of U.S. Pat. No. 5,356,413, specifically incorporated herein by reference, a bone block on the end of a ligament or ligament graft can be suspended from an anchor such as anchor 10 by passing one or more suture threads through transverse opening 22 and connecting those sutures to the bone block by passing the sutures through preformed holes in the bone block. Alternatively, a bone block and ligament graft construct can be more rigidly secured using anchor 10 by using a tape to connect the bone block to the anchor. In this embodiment, a length of tape, such as one-quarter inch polyester tape, can be passed through transverse opening 22 and connected to the bone block at either end of the length of tape. The tape may be connected to the bone block using adhesive and/or tying the tape to the bone block using suture thread.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An anchor for securing soft tissue within a bone tunnel having an inner wall, comprising:

a resilient body member in the form of a circle defining a soft tissue opening and having a longitudinal axis, a first leading end, a second trailing end, and a gap provided in the circle in proximity to the leading end; and at least one bone engaging element connected to the body member;

whereby the anchor is movable between a first, sliding position whereby the at least one bone engaging element slides along the inner wall of the bone tunnel and the anchor is movable within the bone tunnel, and a second, locking position whereby the at least one bone engaging element engages the inner wall of the bone tunnel to resist movement of the anchor within the bone tunnel.

2. The anchor of claim 1, wherein the at least one bone engaging element is connected to the body member at the second trailing end of the body member.

3. The anchor of claim 2, wherein the body member includes a deformable portion in proximity to the at least one bone engaging element, said deformable portion allowing movement of the anchor from the first position to the second position.

4. The anchor of claim 3, wherein the at least one bone engaging element comprises two opposed bone engaging legs.

5. The anchor of claim 4, wherein the bone engaging legs extend at an angle with the longitudinal axis and generally in a direction from the leading to the trailing end of the anchor and outward from the longitudinal axis and extend in a lateral direction transverse to the soft tissue opening.

6. The anchor of claim 5, wherein the deformable portion includes a region of the body member between the connection of each bone engaging leg to the body member.

7. The anchor of claim 6, wherein stabilizing legs are provided on the body member on opposite sides of the gap.

8. The anchor of claim 4, wherein a pull tool engaging element is provided on the second trailing end of the body between the two opposed bone engaging legs.

9. The anchor of claim 1, wherein the anchor is a unitary anchor body with the at least one bone engaging element integrally formed with the anchor body.

10. The anchor of claim 1, wherein the anchor is formed from a bioabsorbable material.

11. The anchor of claim 1, wherein the anchor is configured for movement from the first to the second position in response to tension placed on the soft tissue opening and the engagement of the at least one bone engaging element with the inner wall of the bone tunnel.

12. A bioabsorbable anchor for securing soft tissue within a bone tunnel having an inner wall, comprising:
a resilient body defining a soft tissue opening and having a longitudinal axis, a first leading end and a second trailing end;
two opposed bone engaging legs resiliently connected to the body at the second trailing end and extending at an angle away from the longitudinal axis and in a direction from the leading end to the trailing end; and
a pull tool engaging element provided on the second trailing end of the body between the two opposed bone engaging legs, said pull tool engaging element comprising an opening in the body.

13. The anchor of claim 12, wherein the anchor body is in the form of a circle having a gap located in proximity to the leading end of the anchor body.

14. The anchor of claim 13, wherein stabilizing legs are provided on opposite sides of the gap.

15. The anchor of claim 14, wherein the anchor is a unitary body with the two opposed bone engaging legs integrally formed with the anchor body.

16. The anchor of claim 12, wherein the body includes a deformable portion in a region between the connection of each bone engaging leg to the body, said deformable portion allowing movement of the anchor from a first, sliding position to a second, locking position.

17. An anchor for securing soft tissue within a bone tunnel having an inner wall, comprising:
a resilient body member defining a soft tissue opening and having a longitudinal axis, a first leading end and a second trailing end;
two opposed bone engaging elements connected to the body member; and
a pull tool engaging element provided on the second trailing end of the body member between the two opposed bone engaging elements, said pull tool engaging element comprising an opening in the body member;
whereby the anchor is movable between a first, sliding position whereby the at least one bone engaging element slides along the inner wall of the bone tunnel and the anchor is movable within the bone tunnel, and a second, locking position whereby the at least one bone engaging element engages the inner wall of the bone tunnel to resist movement of the anchor within the bone tunnel.

* * * * *